United States Patent
Wang et al.

(10) Patent No.: US 10,159,668 B2
(45) Date of Patent: Dec. 25, 2018

(54) PHARMACEUTICAL COMPOSITION FOR INHIBITING ALPHA-GLUCOSIDASE

(71) Applicant: Tamkang University, New Taipei (TW)

(72) Inventors: San-Lang Wang, New Taipei (TW); Van-Bon Nguyen, Buon Ma Thuot (TW)

(73) Assignee: TAMKANG UNIVERSITY, New Taipei (TW)

( * ) Notice: Subject to any disclaimer, the term of this patent is extended or adjusted under 35 U.S.C. 154(b) by 0 days.

(21) Appl. No.: 15/894,615

(22) Filed: Feb. 12, 2018

(65) Prior Publication Data

US 2018/0296552 A1   Oct. 18, 2018

(30) Foreign Application Priority Data

Apr. 17, 2017  (TW) .............................. 106112723 A

(51) Int. Cl.
*A61K 31/52* (2006.01)
*A61K 31/495* (2006.01)
*A61K 31/465* (2006.01)
*A61K 35/74* (2015.01)
*A61K 31/22* (2006.01)
*A61K 31/401* (2006.01)

(52) U.S. Cl.
CPC ............ *A61K 31/495* (2013.01); *A61K 31/22* (2013.01); *A61K 31/401* (2013.01); *A61K 31/465* (2013.01); *A61K 31/52* (2013.01); *A61K 35/74* (2013.01)

(58) Field of Classification Search
CPC ...................................................... A61K 31/52
USPC ...................................................... 514/263.1
See application file for complete search history.

*Primary Examiner* — Douglas M Willis
(74) *Attorney, Agent, or Firm* — Chun-Ming Shih

(57) ABSTRACT

A composition for inhibiting α-glucosidase has lower side effects to a user, other than the inhibition of α-glucosidase. The composition comprises adenine, (3-hydroxy-dl-proline, nicotinic acid, (3,6-dioxo-piperazin-2-yl)-acetic acid amide, 2-ethylhexyl heptanoate, and a pharmaceutically compatible salt.

4 Claims, 1 Drawing Sheet

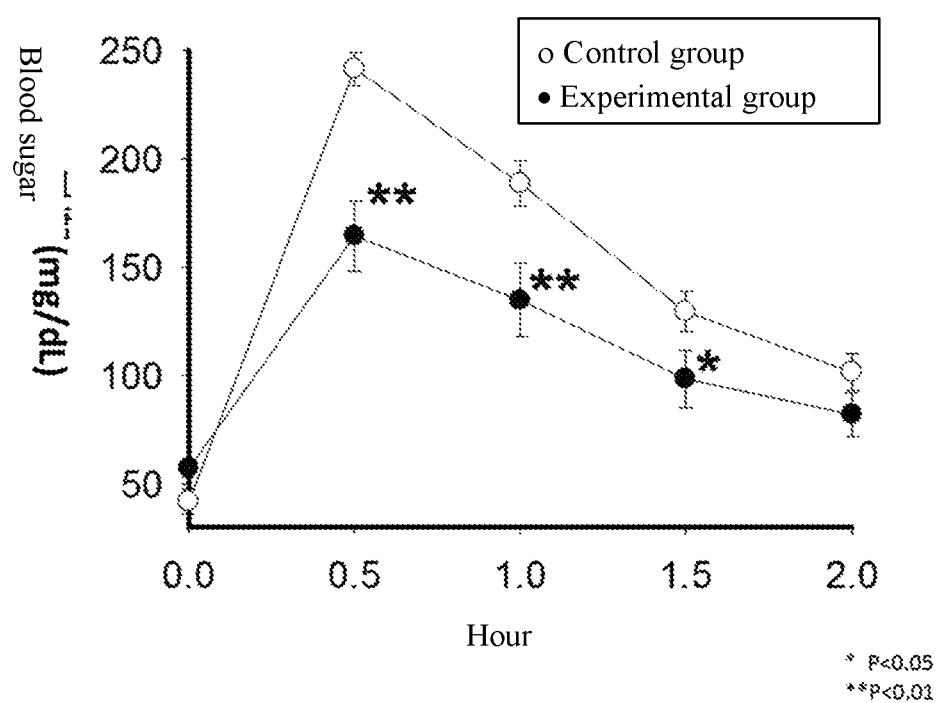

PHARMACEUTICAL COMPOSITION FOR INHIBITING ALPHA-GLUCOSIDASE

BACKGROUND OF THE INVENTION

Field of the Invention

A composition, especially the composition for inhibiting α-glucosidase which applies to patients with Type II diabetes.

Description of Related Art

Diabetes are common diseases of affluence nowadays, and the age of the patients are getting younger. There are two types of diabetes, Type I is a nature autoimmune disease, and Type II is a nurture disease caused by diet and abnormal daily routine. Among the high-risk populations of Type II diabetes, the glucosidase inhibitor is commonly used to inhibit the absorption of saccharides in human body.

α-glucosidase exists in epithelial cells in human small intestine, and facilitates the absorption of glucose in small intestine. The abnormal function of α-glucosidase may cause Type II diabetes, Pompe disease, and Azoospermia.

α-glucosidase inhibitors, abbreviated as α-GI, may reduce the absorption of carbohydrates in human intestinal track. Through the inhibition of α-glucosidase activity and the reduced absorption of carbohydrates in diet, α-GI may reduce high blood sugar after meal, and further become the hypoglycemic drug to treat Type II diabetes. However, the known α-glucosidase inhibitors may have side effects after administration, for example, delaying the digestion and absorption of food, which causes partial indigested food entering colon, and being fermented by gut flora. Furthermore, it causes some discomfort symptoms in stomach, like flatulence and diarrhea.

To solve the aforementioned problems, the inventors prepare a composition for low side effects and an inhibition of α-glucosidase.

BRIEF SUMMARY OF THE INVENTION

The purpose of the present invention is providing a composition, which inhibits α-glucosidase and lower the side effects to the user, to slow down the digestion rate of glucose and to reduce the high blood sugar after meal. Furthermore, the composition may become the inhibitive medicine for the patients of Type II diabetes.

To achieve the aforementioned purpose, the technical feature of the present invention is utilizing the following components to synthesis the composition for inhibiting α-glucosidase, comprising adenine, (3-hydroxy-dl-proline, nicotinic acid, (3,6-dioxo-piperazin-2-yl)-acetic acid amide, 2-ethylhexyl heptanoate, and pharmaceutically compatible salts.

BRIEF DESCRIPTION OF THE SEVERAL VIEWS OF THE DRAWINGS

FIG. 1 indicates the results of inhibiting blood sugar by the composition of the present invention.

DETAILED DESCRIPTION OF THE INVENTION

In order to explain and understand the techniques and procedures of the present disclosure for the examiner's courtesy, the embodiments are illustrated accompanied with figures as following.

Embodiment 1

The present embodiment provides a composition, and the composition comprises adenine, 3-hydroxy-dl-proline, nicotinic acid, (3,6-dioxo-piperazin-2-yl)-acetic acid amide, 2-ethylhexyl heptanoate, and a pharmaceutically compatible salt. The composition is tested to confirm its inhibition of α-glucosidase.

The pharmaceutically compatible salts refer to organic salts and inorganic salts, including but not limited to phosphate, sodium salts, ammonium salts, calcium salts or magnesium salts. More specifically, the pharmaceutically compatible salts include appropriate, non-toxic ammonium, quaternary ammonium salts, and amine cations formed by counter ions, such as halides, hydroxides, carboxylates, hydrosulfates, phosphates, nitrates, C-18 sulfonates, and aromatic sulfonates.

Adenine:

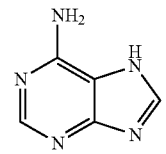

3-hydroxy-dl-proline:

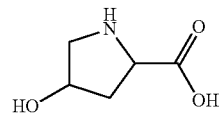

Nicotinic acid:

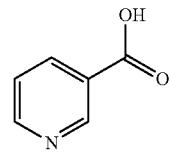

(3,6-dioxo-piperazin-2-yl)-acetic acid amide:

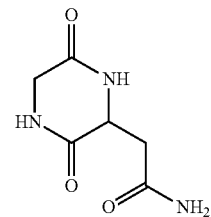 [SMILES: NC(=O)CC1NC(=O)CNC1=O]

2-ethylhexyl heptanoate:

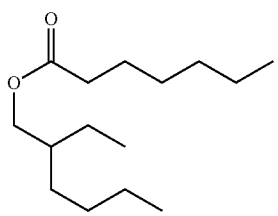 [SMILES: CCCCCCC(=O)OCC(CC)CCCC]

Test of inhibitive activity on a live body

Experimental group: Resolving the composition in distilled water, and feeding it to a mouse. The dosage of the composition is 200 mg/kg, wherein kg refers to the weight of the mouse. Feeding 3 g/kg sucrose to the mouse 25 minutes after the mouse had the composition orally. Having the blood test to detect the blood sugar of the mouse 0.5, 1.5, and 2 hours individually after the mouse had the sucrose.

Control group: Feeding 3 g/kg sucrose to a mouse 25 minutes after the mouse had the same volume of distilled water as the experimental group. Having the blood test to detect the blood sugar of the mouse 0.5, 1.5, and 2 hours individually after the mouse had the sucrose.

Please refer to FIG. 1, it shows that the blood sugar is being inhibited 0.5 hour after taking sucrose, and the efficiency of the inhibition is continuous and steady. In addition, there was no side effects, such as diarrhea, being observed after the mouse took the composition.

Test of IC50

Testing and comparing the inhibitive activity Max % and IC50 of the composition and a known diabetes drug A (α-glucosidase inhibitor) to rat α-glucosidase (abbreviated as Rat aG) and yeast α-glucosidase (abbreviated as Yeast aG), individually. IC50 means the concentration of the inhibitor to achieve 50% inhibition rate.

Please refer to Table 1, the max inhibition rate of the composition to Rat aG is 89%, and IC50 is 101 μg/ml; and the max inhibition rate of the composition to Yeast aG is 98%, and IC50 is 81 μg/ml. The max inhibition rate of the diabetes drug A to Rat aG is 88%, and IC50 is 107 μg/ml; and the max inhibition rate of the diabetes drug A to Yeast aG is 70%, and IC50 is 1395 μg/ml. The composition has the inhibitive activity pretty much the same as the diabetes drug A, and the composition has lower IC50. Therefore, a lower concentration of the composition may achieve the efficiency to inhibit α-glucosidase in the application.

TABLE 1

|   | Rat aG | | Yeast aG | |
| --- | --- | --- | --- | --- |
|   | Max (%) | IC50 (μg/mL) | Max (%) | IC50 (μg/mL) |
| Composition | 89 ± 4 | 101 ± 5.1 | 92 ± 3.2 | 81 ± 4.3 |
| A | 88 ± 3 | 107 ± 5.5 | 70 ± 2.6 | 1395 ± 5 |

Embodiment 2

The present embodiment tests IC50 of adenine, 3-hydroxy-dl-proline, nicotinic acid, (3,6-dioxo-piperazin-2-yl)-acetic acid amide, 2-ethylhexyl heptanoate, and the diabetes drug A to Rat aG and Yeast aG, individually.

Please refer to Table 2, IC50 of the diabetes drug A to Rat aG is 115 μg/ml. IC50 of the diabetes drug A to Yeast aG is 1095 μg/ml. IC50 of nicotinic acid in the present composition to Rat aG is 67 μg/ml. IC50 of (3,6-dioxo-piperazin-2-yl)-acetic acid amide and 2-ethylhexyl heptanoate to Yeast aG is 4.0 μg/ml. Hence, a lower concentration of the composition may achieve the efficiency to inhibit α-glucosidase in the application.

TABLE 2

| Component | Rat aGI | Yeast aGI |
| --- | --- | --- |
| Adenine | — | 21.5 |
| 3-hydroxy-dl-proline | 100 | 5.3 |
| (3,6-dioxo-piperazin-2-yl)-acetic acid amide | 105 | 4.0 |
| 2-ethylhexyl heptanoate | 105 | 4.0 |
| Nicotinic acid | 67 | 517 |
| Diabetes medicine A | 115 | 1095 |

Embodiment 3

The composition of the present invention is extracted from a supernatant from DSM 32521 *Paenibacillus* incubated in a culture medium under 25° C. to 37° C. for three days.

The carbon/nitrogen source of DSM 32521 *Paenibacillus* of the present embodiment is 100 ml culture medium containing 0.8% nutrient broth, 100 ml culture medium containing 1% shrimp head powder, 0.1% $K_2HPO_4$, and 0.05% $MgSO_4 \cdot 7H_2O$, and 100 ml culture medium containing 1% squid pen powder, 0.1% $K_2HPO_4$, and 0.05% $MgSO_4 \cdot 7H_2O$.

To summarize the aforementioned descriptions, the composition of the present invention may inhibit α-glucosidase in intestinal track, and lower digestive rate of saccharides to reduce the blood sugar after meal.

The aforementioned descriptions are preferred embodiments of the present disclosure, and do not limit the scope of the present disclosure. Therefore, simple and equivalent variation and revision based on the present claim scope and the contents of present specification would fall within the claim scope of the present disclosure.

DEPOSIT OF BIOLOGICAL MATERIAL

Deposit Information
Leibniz Institute DSMZ-German Collection of Microorganisms and Cell Cultures (DSMZ)
Oct. 27, 2016, DSM 32521
Food Industry Research and Development Institute of Bioresource Collection and Research Center (BCRC)
Oct. 27, 2016, BCRC 910751

The invention claimed is:

1. A pharmaceutical composition, comprising adenine, 3-hydroxyproline, nicotinic acid, (3,6-dioxopiperazin-2-yl) acet amide, 2-ethylhexyl heptanoate, and a pharmaceutically acceptable salt selected from the group consisting of an ammonium halide salt, an ammonium hydroxide salt, an ammonium carboxylate salt, an ammonium bisulfate salt, an ammonium phosphate salt, an ammonium nitrate salt, an ammonium sulfonate salt, a sodium halide salt, sodium hydroxide, a sodium carboxylate salt, sodium bisulfate, sodium phosphate, sodium nitrate, a sodium sulfonate salt, a calcium halide salt, calcium hydroxide, a calcium carboxylate salt, calcium bisulfate, calcium phosphate, calcium nitrate, a calcium sulfonate salt, a magnesium halide salt, magnesium hydroxide, a magnesium carboxylate salt, magnesium bisulfate, magnesium phosphate, magnesium nitrate and magnesium salt.

2. A method for inhibiting α-glucosidase activity in a subject, comprising administering to a subject in need thereof a pharmaceutical composition comprising adenine, 3-hydroxyproline, nicotinic acid, (3,6-dioxopiperazin-2-yl)acetamide, 2-ethylhexyl heptanoate, and a pharmaceutically-acceptable salt selected from the group consisting of an ammonium halide salt, an ammonium hydroxide salt, an ammonium carboxylate salt, an ammonium bisulfate salt, an ammonium phosphate salt, an ammonium nitrate salt, an ammonium sulfonate salt, a sodium halide salt, sodium hydroxide, a sodium carboxylate salt, sodium bisulfate, sodium phosphate, sodium nitrate, a sodium sulfonate salt, a calcium halide salt, calcium hydroxide, a calcium carboxylate salt, calcium bisulfate, calcium phosphate, calcium nitrate, a calcium sulfonate salt, a magnesium halide salt, magnesium hydroxide, a magnesium carboxylate salt, magnesium bisulfate, magnesium phosphate, magnesium nitrate and a magnesium salt.

3. The method of claim 2, wherein the inhibition of α-glucosidase activity occurs in the intestinal track of the subject.

4. The method of claim 2, wherein the inhibition of α-glucosidase activity reduces the rate of saccharide digestion in the subject.

* * * * *

UNITED STATES PATENT AND TRADEMARK OFFICE
CERTIFICATE OF CORRECTION

PATENT NO.       : 10,159,668 B2
APPLICATION NO.  : 15/894615
DATED            : December 25, 2018
INVENTOR(S)      : San-Lang Wang and Van-Bon Nguyen Page 1 of 1

It is certified that error appears in the above-identified patent and that said Letters Patent is hereby corrected as shown below:

On the Title Page

Item [72], Change "Van-Bon Nguyen, Buon Ma Thuot (TW)" to --Van-Bon Nguyen, Buon Ma Thuot City (VN)--

Signed and Sealed this
Twenty-first Day of May, 2019

Andrei Iancu
*Director of the United States Patent and Trademark Office*